United States Patent [19]

Kai et al.

[11] Patent Number: 5,057,623

[45] Date of Patent: Oct. 15, 1991

[54] ORGANIC FLUORINE COMPOUND

[75] Inventors: Yoshiaki Kai, Neyagawa; Takashi Suzuki, Takatsuki, both of Japan

[73] Assignee: Matsushita Electric Industrial Co., Ltd., Osaka, Japan

[21] Appl. No.: 420,876

[22] Filed: Oct. 13, 1989

[30] Foreign Application Priority Data

| Oct. 14, 1988 | [JP] | Japan | 63-260079 |
| Oct. 14, 1988 | [JP] | Japan | 63-260080 |
| Nov. 29, 1988 | [JP] | Japan | 63-301151 |
| Nov. 29, 1988 | [JP] | Japan | 63-301152 |
| Dec. 9, 1988 | [JP] | Japan | 63-312298 |
| Dec. 9, 1988 | [JP] | Japan | 63-312306 |

[51] Int. Cl.$^5$ ............... C07C 211/08; C07C 211/07
[52] U.S. Cl. .................... 564/82; 564/90; 564/92; 564/94; 564/96; 564/97; 564/153; 564/157; 564/183; 564/185; 564/209; 564/212; 564/353; 564/354; 564/374; 564/384; 564/389; 564/504; 564/508; 564/509; 564/510
[58] Field of Search ............ 564/82, 90, 92, 94, 564/96, 97, 153, 157, 183, 185, 209, 212, 353, 354, 374, 384, 389, 504, 508, 509, 510

[56] References Cited

U.S. PATENT DOCUMENTS

| 2,395,336 | 2/1946 | MacMullen et al. | 564/389 X |
| 2,416,265 | 2/1947 | MacMullen et al. | 564/389 X |
| 2,691,043 | 10/1954 | Husted et al. | 564/510 X |
| 2,782,184 | 2/1957 | Husted et al. | 564/510 X |
| 2,832,795 | 4/1958 | Hempel et al. | 564/389 X |
| 3,171,861 | 3/1965 | Ablbrecht | 260/633 |
| 3,419,595 | 12/1968 | Hansen | 564/510 |
| 4,059,629 | 11/1977 | Foulletier et al. | 564/510 X |

FOREIGN PATENT DOCUMENTS 379067 6/1957 Japan .
63-45238 2/1988 Japan .

Primary Examiner—Richard L. Raymond
Attorney, Agent, or Firm—Stevens, Davis, Miller & Mosher

[57] ABSTRACT

An organic fluorine compound represented by the general formula

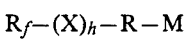

wherein $R_f$ is a group selected from the following (a) and (b);

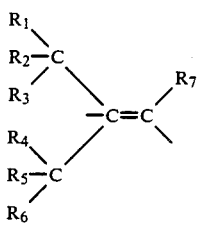

and

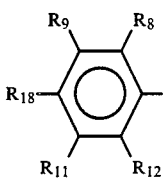

$R_9$-$R_{12}$: F, $C_nF_{2n+1}$ (n = 1-3),

X denotes a linking group selected from —O—, —S—, and —COO—, h denotes 0 or 1, R is a hydrocarbon chain comprising a phenylene group having an alkylene group with a total carbon number of 10 or more, or the derivative thereof, or an aliphatic alkylene group of a carbon number of 10 or more, and M is a group selected from —OH, —COOH, —SH, and —CONH$_2$.

The organic fluorine compound of the present invention greatly improves the dispersibility of magnetic powders in magnetic coating materials, has also an excellent rust prevention effect on metallic magnetic powders, and exhibits a marked dispersing effect even on fluorocarbon resin fine powders, which can be difficultly dispersed with conventional dispersing agents.

1 Claim, 1 Drawing Sheet

ORGANIC FLUORINE COMPOUND

BACKGROUND OF THE INVENTION

1. Field of the Invention

The present invention relates to an organic fluorine compound suitable as a dispersing agent for dispersing fine particles of various metals, metal oxides, metal salts, fluorocarbons, fluorine-containing resins, and the like into various resins or the solutions thereof. More particularly, it relates to an organic fluorine compound which is capable of imparting such properties as water repellency, oil repellency, soil resistance, mold release, and rust prevention to the surface of articles obtained from such dispersions and is particularly excellent in dispersion stability.

2. Description of the Prior Art

A ferromagnetic metal film type magnetic recording medium obtained by forming a magnetic layer of cobalt, nickel, iron or an alloy comprising said metals as the principal component by a vacuum film-forming process, such as vacuum vapor deposition, sputtering and ion plating, on a substrate, e.g. a film of polymer such as polyester and polyimide, aluminum alloy sheet, glass sheet, etc. can potentially have a drastically increased recording density. To realize such increased density, however, it is necessary to make the magnetic layer very thin and at the same time to make the surface of the medium as flat as possible. However, since these measures act toward lowering the endurance reliability of said medium, a variety of measures have been investigated with the aim of improving the endurance reliability. For example, in a magnetic disc unit used in the external memory of electronic computers, a so-called contact-start-stop (CSS) system is in use wherein generally the magnetic head floats above the magnetic disc surface when the disc is in operation and contacts with the disc surface when the disc stops. For such a system, a method has been proposed wherein fine irregularities (protruded parts) are formed on the disc surface, a ferromagnetic metal thin film is then formed thereon, and a protective layer and a lubricant layer are further provided on the ferromagnetic metal thin film, the protective layer comprising graphite, SiO$_2$ etc. as the main component and the lubricant layer comprising a perfluoropolyether having modified or unmodified molecular terminals.

In magnetic coating materials used in magnetic tapes, magnetic discs, magnetic cards, etc., the dispersibility and the dispersion stability of ferromagnetic fine particles are important factors in manifestation of magnetic properties. Further, when ferromagnetic metal fine particles comprising iron, its alloy, or the like is used as such ferromagnetic fine particles, the storage stability after magnetic coating formation, viewed from the point of rust prevention, is also a important factor. Previously, therefore, hydrocarbons having polar groups, e.g. higher fatty acids or their sulfuric esters, lecithin, and aliphatic phosphoric acid esters, have been used as as surface active agent with the aim of enhancing dispersibility or storage stability.

In order to increase the recording density of a ferromagnetic metal thin film type magnetic recording medium, it is necessary to reduce the floating distance of the magnetic head. In such a case, if the surface configuration of the magnetic disc is improved by reducing the height of protruded parts on the disc surface, it causes lowering of CSS durability and at the same time causes a so-called adsorption phenomenon wherein the lubricant on the disc surface gathers between the magnetic head and the disc during stoppage of the disc unit and resultantly the magnetic head sticks to the disc surface. To solve such problems, therefore, it is important that the lubricant on the disc surface forms a coating layer composed of the lubricant on the protective layer surface and can be easily sheared between the lubricant molecules at the contact point of these coating layers, namely at the sliding surface between the disc and the magnetic head. Since a perfluoropolyether used as a lubricant is covered over almost the whole surface of its molecule with fluorine atoms, it shows a good shearing property between molecules but a weak adhesive force to the disc surface or the magnetic head surface. Although introduction of various polar groups into perfluoropolyether has been proposed to strengthen the adhesive force to the magnetic head surface, the effect of the introduction of polar groups is not satisfactory because perfluoropolyether has itself a high molecular weight of at least 3000, usually 4000 or more, and the effect of improving disc durability is also not marked. On the other hand, when the molecular weight of perfluoropolyether itself is decreased in order to enhance the efficacy of polar groups, it leads to spin-out due to high speed rotation of the disc and vaporization of the polyether itself because interaction between the molecules is weak. Accordingly, reduction of the molecular weight is difficult to adopt in practice.

On the other hand, aliphatic hydrocarbons having polar groups typically represented by stearic acid are excellent in adhesive strength to various surfaces and in disposition toward molecular orientation. However, since they show a stronger interaction between molecules as compared with fluorohydrocarbons, they can hardly give a desired durability when used as the lubricant.

Further, surface active agents for magnetic coating materials previously used have a limitation in their dispersibility and, since the surface roughness of the magnetic layer is determined by the dispersibility, they not only are becoming incapable of meeting the recent demand for higher recording density but have difficulties in that these surface active agents bleed out gradually to the magnetic layer surface to deteriorate the practical performance or cause rusting during storage at high temperature to deteriorate the performance.

SUMMARY OF THE INVENTION

The object of the present invention is to provide an organic fluorine compound which can solve the difficulties mentioned above.

The organic fluorine compound of the present invention is represented by the general formula

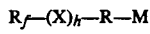

wherein $R_f$ is a fluorohydrocarbon group, R is a hydrocarbon group, and X and M are each a functional group.

In the organic fluorine compound of the present invention, the functional group participates in physical or chemical bonding with fine particles of various metals, metal oxides, metal salts, etc. and in manifestation of affinity for polar groups present in the resin and solvent of the coating material, and the fluorohydrocarbon group participates in modification of the coating film surface properties and in uniformalization of dispersion.

BRIEF DESCRIPTION OF THE DRAWING

The attached drawing is a sectional view showing the structure of a magnetic recording medium using an organic fluorine compound according to one embodiment of the present invention.

PREFERRED EMBODIMENT

EXAMPLES

EXAMPLE 1

Figure 1:
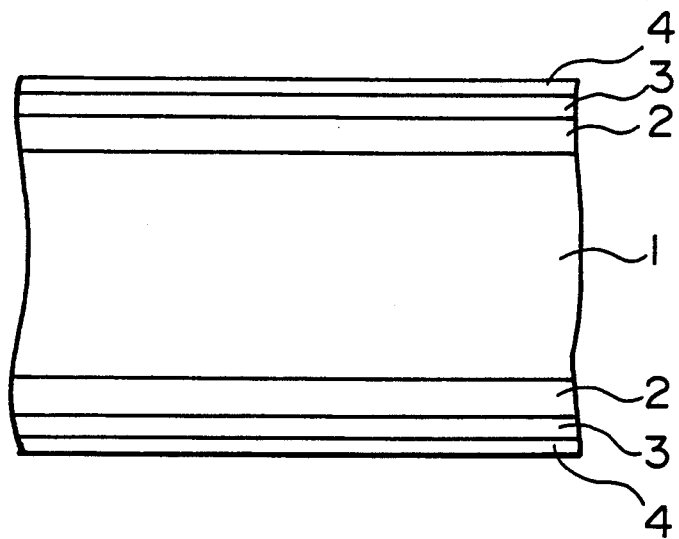

In the surface active agent according to the present invention, the fluoroalkyl terminal group may be, for example, $C_nF_{2n+1}-$, $HCF_2(CF_2)_n-$, and $C_nF_{2n-1}-$, wherein n is an integer of 3 or more, and may be any of straight-chain or branched-chain, saturated or unsaturated one; the fluoroaryl terminal group may be, for example,

[structure: pentafluorophenyl group], and

[structure: bis(pentafluorophenyl)methyl group] CH—;

the aliphatic alkylene group may be, for example, $-C_nH_{2n}-$, $-C_nH_{2n-2}-$, $-C_nH_{2n-4}-$, and $-C_kH_{2k}-CH-C_mH_{2m}-$,
$\quad\quad\quad\quad\; |$
$\quad\quad\quad\; C_lH_{2l+1}$ wherein n is an integer of 10 or more, and k, l and m are each an integer of 1 or more, with the proviso that k+l+m is an integer of 10 or more;

the phenylene group having an alkylene group may be for example,

[structure: phenylene with substituents $(C_mH_{2m+1})_l$ and $-C_nH_{2n}-$]

wherein l is an integer of 0–4, and m and n are each an integer of 1 or more, provided that $1 \times m+n+6$ is an integer of 10 or more;

the fluoroalkyl terminal group or the fluoroaryl terminal group are linked with the aliphatic alkylene group or the phenylene group having an alkylene group directly or through various linking groups exemplified below $-O-$, $-S-$, $-COO-$, $-CON-$, and $-SO_2N-$,
$\quad\quad\quad\quad\quad\quad\quad\quad\quad\; |\quad\quad\quad\quad\quad\; |$
$\quad\quad\quad\quad\quad\quad\quad\quad\quad R\quad\quad\quad\quad\; R$ wherein R denotes H, $CH_3$ or $C_2H_5$.

The fluorohydrocarbon chains linked as described above are linked with functional groups directly or through various linking groups exemplified below $-O-(CH_2)_n-$, $-S-(CH_2)_n-$, $-COO-(CH_2)_n-$, $-CON-(CH_2)_n-$, and
$\quad\quad\quad\quad\quad\quad\quad\quad\quad\; |$
$\quad\quad\quad\quad\quad\quad\quad\quad\; R$ $-SO_2N-(CH_2)_n-$,
$\quad\; |$
$\quad R$ wherein n denotes an integer of 1 or more, and R denotes H, $CH_3$ or $C_2H_5$.

Suitable fluoroalkyl terminal groups are those having a carbon number of 3 or more, preferably 5 or more. Those of a carbon number of 2 or less do not give a good dispersibility and rust prevention effect.

Suitable fluoroaryl terminal groups are fluorophenyl groups, fluorobiphenylyl groups, and the derivatives thereof. Suitable hydrocarbon chains are aliphatic alkylene groups and phenylene groups having an alkylene group both having a number of total carbon atoms of 10 or more, preferably 12 or more, and the derivatives thereof. When the number of total carbon atoms is 9 or less good dispersibility and rust prevention effect cannot be obtained. The ratio of the atomic group weight of the fluoroalkyl group or the fluoroaryl group to the molecular weight of the surface active agent molecule is desirably in the range of 10–90%, preferably 20–80%. When the ratio is outside the above range, the dispersion stability is poor.

EXAMPLE 2

Preparation of a Long-Chain Alkylcarboxylic Acid Having a Fluoroalkyl Terminal Group The long-chain alkylcarboxylic acid having a fluoroalkyl terminal group can be prepared by heating a monohaloalkylcarboxylic acid ester having a fluoroalkyl derivative residue represented by the formula $R_f-CH_2CHX-R-COOC_nH_{2n+1}$, wherein $R_f$ is a straight-chain or braunched-chain, saturated or unsaturated, fluoroalkyl derivative residue of 3 or more carbon atoms, X is a halogen atom other than that of fluorine, R is a straight-chain or braunched-chain, saturated or unsaturated, aliphatic alkylene group of 1 or more carbon atoms, n is an integer of 1 or more, and the number of total carbon atoms in the hydrocarbon moiety of the fluoroalkyl derivative residue, the aliphatic alkylene group, and the monohaloalkylene group ($-CH_2CHX-$) is 10 or more, obtainable by reacting a halide having a fluoroalkyl derivative residue with a carboxylic acid ester having an ω-alkenyl group in the presence of an organic peroxide, with zinc dust in hydrochloric acid/ethanol to effect dehalogenation and hydrogenation, and then hydrolyzing the ester moiety with 90% alcoholic alkali solution. A long-chain alkylcarboxylic acid having a fluoroaryl terminal group and like compounds can also be prepared in the same manner as above.

EXAMPLE 3

Preparation of 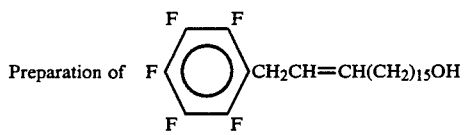

In a 1-l round-bottomed flask were placed 61.6 g (0.20 mol) of pentafluorobenzyl iodide represented by the formula

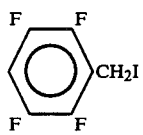

and 50.5 g (0.20 mol) of 16-heptadecyn-1-ol, CH≡C(CH$_2$)$_{15}$OH, the mixture was then heated to 130° C., and 1 g of di(tert-butyl) peroxide was added dropwise thereto with stirring over a period of about 20 minutes. Succeedingly, stirring was continued at 130°-140° C. for 6 hours to complete the reaction. The reaction product was recrystallized with methanol to obtain a brown solid represented by the formula

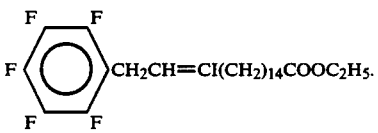

Then, 84.1 g (0.15 mol) of the solid and 300 ml of ethanol containing about 30% of hydrogen chloride were placed in a 1-l round-bottomed flask, then heated to 70° C., and 30 g of zinc dust was carefully and gradually added thereto with stirring. Succeedingly, stirring was continued at 70°-75° C. for 4 hours to complete the reaction. After filtering off the zinc dust, the reaction liquid was transferred to a separatory funnel containing 1 l of distilled water and the reaction product was extracted with 1 l of ethyl acetate. After 1 l of water was discarded, the ethyl acetate solution was washed repeatedly with distilled water until the pH of the aqueous layer reached 7. The ethyl acetate solution was dried with anhydrous sodium sulfate, the solvent was distilled off under reduced pressure, and the resulting product was recrystallized with acetone to obtain a white solid represented by the formula

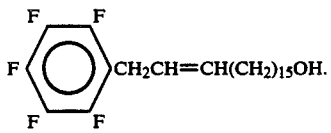

The solid was found, based on infrared spectroscopy, GPC, organic mass spectrometry, etc., to be a single component containing no starting material, no intermediate product and no by-product.

EXAMPLE 4

Preparation of 

In a 1 l round-bottomed flask were placed 61.6 g (0.20 mol) of pentafluorobenzyl iodide represented by the formula

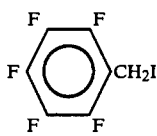

and 58.9 g (0.20 mol) of ethyl 16-heptadecinoate of the formula

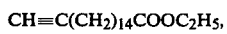

the mixture was heated to 130° C., and 1 g of di(tert-butyl) peroxide was added dropwise thereto with stirring over a period of about 20 minutes. Succeedingly, stirring was continued at 130°-140° C. for 6 hours to complete the reaction. The reaction product was recrystallized with methanol to obtain a brown solid represented by the formula

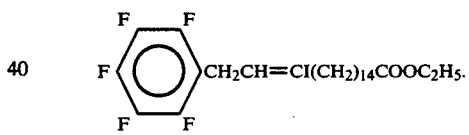

Then, 90.4 g (0.15 mol) of the solid and 300 ml of ethanol containing about 30% of hydrogen chloride were placed in a 1-l round-bottomed flask, then heated to 70° C., and 30 g of zinc dust was carefully and gradually added thereto with stirring. Succeedingly, stirring was continued at 70°-75° C. for 4 hours to complete the reaction. After filtering off the zinc dust, the reaction liquid was transferred to a separatory funnel containing 1 l of distilled water and the reaction product was extracted with 1 l of ethyl acetate. After 1 l of water was discarded, the ethyl acetate solution was washed repeatedly with distilled water until the pH of the aqueous layer reached 7. The ethyl acetate solution was dried with anhydrous sodium sulfate, the solvent was distilled off under reduced pressure, and the resulting product was recrystallized with ethanol to obtain a white solid represented by the formula

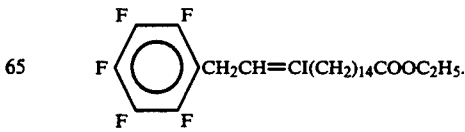

Then, 47.7 g (0.10 mol) of the solid and 300 ml of 90% ethanol were placed in a 1-l round-bottomed flask and 20 g of potassium hydroxide was gradually added thereto with stirring at room temperature. Succeedingly, stirring was continued at 60°–70° C. for 3 hours to complete the reaction. The reaction liquid was acidified by dropwise addition of 10% hydrochloric acid, whereupon a precipitate was formed. The precipitate was collected by filtration, transferred to a separatory funnel containing 1 l of ethyl acetate, and dissolved. The resulting solution was washed repeatedly with distilled water until the pH of the aqueous layer reached 7. The ethyl acetate solution was dried with anhydrous sodium sulfate and recrystallized to obtain a white solid represented by the formula

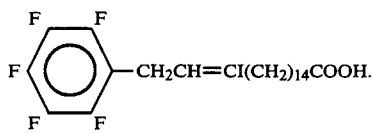

The solid was found, based on infrared spectroscopy, GPC, organic mass spectrometry, etc., to be a single component containing no starting material, no intermediate product, and no by-product.

EXAMPLE 5

Preparation of a Secondary Long-Chain Alkylcarboxylic Acid Amide Having a Fluoroalkyl Terminal Group Said compound can be prepared by reacting an alkylcarboxylic acid chloride having a fluoroalkyl derivative residue or an alkylcarboxylic acid anhydride having a fluoroalkyl derivative residue with an alkylamine having a fluoroalkyl derivative residue in the presence of a base such as triethylamine and pyridine. The compound can also be obtained through a double-layer reaction of an organic solvent layer containing said acid chloride or said acid anhydride and said amine and an aqueous alkali solution layer.

EXAMPLE 6

Preparation of $C_8F_{17}(CH_2)_{10}CONH(CH_2)_{12}(CF_2)_9CF_2H$

In a 1-l round-bottomed flask were placed carefully 124.6 g (0.20 mol) of heptadecafluorononadecanoic acid chloride, $C_8F_{17}(CH_2)_{10}COCl$, and 137.1 g (0.20 mol) of ω-H-eicosafluoro-n-docosanamine, $HCF_2(CF_2)_9(CH_2)_{12}NH_2$, then 100 ml of benzene was added thereto, and the mixture was cooled to 10°–15° C. Then 300 ml of 10% aqueous sodium hydroxide solution was added dropwise with stirring over a period of about 2 hours. Subsequently, stirring was continued at room temperature for 6 hours to complete the reaction. The reaction liquid was mixed with 1 l of ethyl acetate, and the organic layer was separated and washed repeatedly with distilled water until the pH of the aqueous layer reached 7. The ethyl acetate solution was dried with anhydrous sodium sulfate, the solvent was distilled off under reduced pressure, and the resulting product was recrystallized with ethanol to obtain a white solid represented by the formula $C_8F_{17}(CH_2)_{10}CONH(CH_2)_{12}(CF_2)_9CF_2H.$ The solid was found, based on infrared spectroscopy, GPC, organic mass spectrometry, etc., to be a single component containing no starting material and no by-product.

EXAMPLE 7

Preparation of 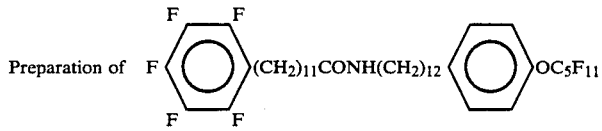

In a 1-l round-bottomed flask was placed 77.0 g (0.20 mol) of ω-perfluorobenzyl-n-dodecanoic acid chloride,

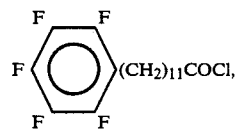

and cooled to 10°–15° C. Then, 100 ml of benzene containing 47.5 g of pyridine and 111.5 g (0.20 mol) of a fluoroamine represented by the formula

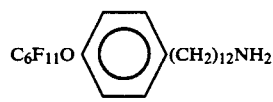

was added dropwise thereto with stirring over a period of about 2 hours. Thereafter, stirring was continued at room temperature for 6 hours to complete the reaction. The reaction liquid was mixed with 1 l of ethyl acetate, then washed with 5% aqueous hydrochloric acid solution, and further washed repeatedly with distilled water until the pH of the aqueous layer reached 7. The ethyl acetate solution was dried with anhydrous sodium sulfate, the solvent was distilled off under reduced pressure, and the resulting product was recrystallized with methanol to obtain a white solid represented by the formula

The solid was found, based on infrared spectroscopy, GPC, organic mass spectrometry, etc., to be a single component containing no starting material and no by-product.

EXAMPLE 8

Preparation of

-continued

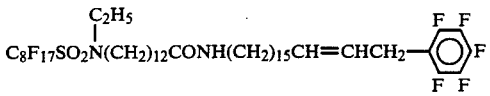

In a 1-1 round-bottomed flask was placed 151.6 g (0.20 mol) of a fluorocarboxylic acid chloride represented by the formula

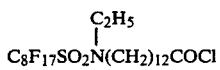

and cooled to 10°–15° C. Then, 100 ml of benzene containing 47.5 g of pyridine and 86.7 g (0.20 mol) of a fluoroamine represented by the formula

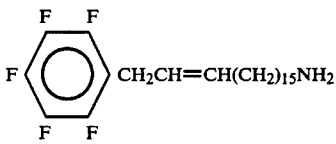

was added dropwise thereto with stirring over a period of about 2 hours. Thereafter, stirring was continued at room temperature for 6 hours to complete the reaction. The reaction liquid was mixed with 1 l of ethyl acetate, then washed with 5% aqueous hydrochloric acid solution, and further washed repeatedly with distilled water until the pH of the aqueous layer reached 7. The ethyl acetate solution was dried with anhydrous sodium sulfate, the solvent was distilled off under reduced pressure, and the resulting product was recrystallized with methanol to obtain a white solid represented by the formula

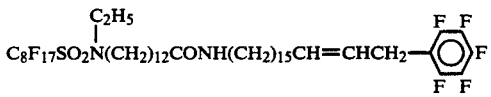

The solid was found, based on infrared spectroscopy, GPC, organic mass spectrometry, etc., to be a single component containing no starting material and no by-product.

EXAMPLE 9

Preparation of 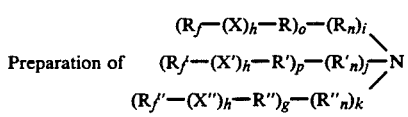

The primary amine can be prepared by reducing an acid amide obtainable by the reaction of a carboxylic acid chloride having a fluoroalkyl derivative residue with ammonia with borane-tetrahydrofuran complex ($BH_3$.THF). The secondary amine can be prepared by reducing with $BH_3$.THF an acid amide obtainable by the reaction of a carboxylic acid chloride having a fluoroalkyl derivative residue or an aliphatic or aromatic carboxylic acid chloride with a primary amine having a fluoroalkyl derivative residue or an aliphatic or aromatic primary amine. The tertiary amine can be prepared by reacting a secondary amine having a fluoroalkyl derivative residue or an aliphatic or aromatic secondary amine with a halogenide having a fluoroalkyl derivative residue or an aliphatic or aromatic halogenide with the aid of sodium carbonate or potassium carbonate.

EXAMPLE 10

Preparation of $C_8F_{17}(CH_2)_{11}NH_2$

In a 1-1 round-bottomed flask was placed 124.6 g (0.20 mol) of heptadecafluorononadecanoic acid chloride, $C_8F_{17}(CH_2)_{10}COCl$, and cooled to 10°–15° C. Then, a mixed solution of 25.1 g of an about 28% aqueous ammonia solution and 47.5 g of pyridine was added dropwise thereto with stirring, over a period of about 2 hours. Thereafter, stirring was continued at room temperature for 6 hours to complete the reaction. The reaction liquid was mixed with 1 l of ethyl acetate, then washed with 5% aqueous hydrochloric acid solution, and further washed repeatedly with distilled water until the pH of the aqueous layer reached 7. The ethyl acetate solution was dried with anhydrous sodium sulfate, the solvent was distilled off under reduced pressure, and the resulting product was recrystallized with methanol to obtain heptadecafluoronoadecanoic acid amide. In a 1-1 round-bottomed flask were placed 60.3 g (0.10 mol) of the acid amide and 300 ml of THF, and 120 ml (0.12 mol) of 1 molar $BH_3$.THF/THF solution was added dropwise thereto with stirring at room temperature in about 1 hour while high purity nitrogen gas was being passed through the flask. Thereafter, stirring was continued at room temperature for 7 hours to complete the reaction. Then, 100 ml of water was carefully added dropwise to the reaction liquid to effect hydrolysis, and 50 ml of 6N hydrochloric acid was further added. The reaction liquid was then heated to 85°–90° C. to distill THF away in atmospheric air, and 100 ml of 6N sodium hydroxide solution was added to the liquid to isolate the produced amine. The amine was extracted three times with 300 ml of ether in all. The extract was washed repeatedly with distilled water until the pH of the aqueous layer reached 7, then dried with anhydrous sodium sulfate, and the solvent was distilled off under reduced pressure. The resulting product was recrystallized with methanol to obtain a white solid represented by the formula $C_8F_{17}(CH_2)_{11}NH_2$. The solid was found, based on GPC and organic mass spectrometry, to be a single component containing no starting material and n intermediate product.

EXAMPLE 11

Preparation of 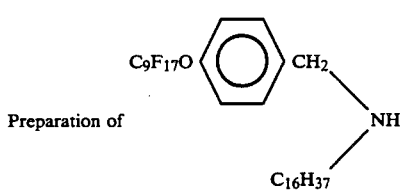

In a 1 l round-bottomed flask was placed 117.3 g (0.20 mol) of a fluorocarboxylic acid chloride represented by the formula

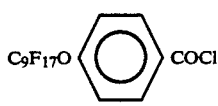

and then cooled to 10°-15° C. Then a mixed solution of 53.9 g (0.20 mol) of stearylamine and 47.5 g of pyridine was added dropwise thereto with stirring over a period of about 2 hours. Thereafter, stirring was continued at room temperature for 6 hours to complete the reaction. The reaction liquid was mixed with 1 l of ethyl acetate, then washed with 5% aqueous hydrochloric acid solution, and further washed repeatedly with distilled water until the pH of the aqueous layer reached 7. The ethyl acetate solution was dried with anhydrous sodium sulfate, and the solvent was distilled away under reduced pressure. The resulting product was recrystallized with methanol to obtain a fluorocarboxylic acid amide represented by the formula

Then, 82.0 g (0.10 mol) of the acid amide and 300 ml of THF were placed in a 1 l round-bottomed flask, and 120 ml (0.12 mol) of 1 molar $BH_3 \cdot THF/THF$ solution was added dropwise thereto with stirring at room temperature in about 1 hour while high purity nitrogen gas was being passed through the flask. Thereafter, stirring was continued at room temperature for 7 hours to complete the reaction. Then, 100 ml of water was carefully added dropwise to the reaction liquid to effect hydrolysis, and 50 ml of 6N hydrochloric acid was further added. The reaction liquid was then heated to 85°-90° C. to distill THF away in atmospheric air, and 100 ml of 6N sodium hydroxide solution was added to the liquid to isolate the produced amine. The amine was extracted three times with 300 ml of ether in all. The extract was washed with distilled water repeatedly until the pH of the aqueous layer reached 7, then dried with anhydrous sodium sulfate, and the solvent was distilled away under reduced pressure. The resulting product was recrystallized with methanol to obtain a white solid represented by the formula

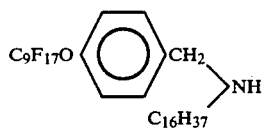

The solid was found, based on GPC and organic mass spectrometry, to be a single component containing no starting material and no intermediate product.

EXAMPLE 12

Preparation of
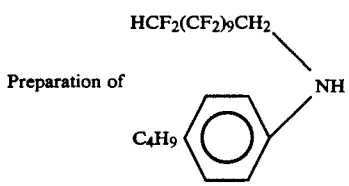

In a 1 l round-bottomed flask were placed 29.9 g (0.20 mol) of 4-n-butylaniline and 300 ml of 10% aqueous sodium hydroxide solution, and 106.2 g (0.20 mol) of 11H-eicosafluoroundecanoic acid chloride, $HCF_2(CF_2)_9COCl$, was added dropwise to the mixture with stirring at room temperature over a period of about 2 hours. Succeedingly, stirring was continued at room temperature for 6 hours to complete the reaction. The reaction liquid was mixed with 1 l of ethyl acetate, then washed with 5% aqueous hydrochloric acid solution, and further washed repeatedly with distilled water until the pH of the aqueous layer reached 7. The ethyl acetate solution was dried with anhydrous sodium sulfate and the solvent was distilled away under reduced pressure. The resulting product was recrystallized with ethanol to obtain a fluorocarboxylic acid amide represented by the formula

Then, 65.9 g (0.10 mol) of the acid amide and 300 ml of THF were placed in a 1 l round-bottomed flask, and 120 ml (0.12 mol) of 1 molar $BH_3 \cdot THF/THF$ solution was added dropwise thereto with stirring at room temperature for about 1 hour while high purity nitrogen gas was being passed through the flask. Thereafter, stirring was continued at room temperature for 7 hours to complete the reaction. Then, 100 ml of water was carefully added dropwise to the reaction liquid to effect hydrolysis, and 50 ml of 6N hydrochloric acid was further added. The reaction liquid was then heated to 85°-90° C. to distill THF away in atmospheric air, and 100 ml of 6N sodium hydroxide solution was added to the liquid to isolate the produced amine. The amine was extracted three times with 300 ml of ether in all. The extract was washed with distilled water repeatedly until the pH of the aqueous layer reached 7. The resulting product was recrystallized with methanol to obtain a white solid represented by the formula

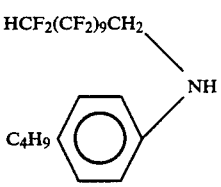

The results of GPC and organic mass spectrometry revealed that the product was a single component containing no starting material and no intermediate product.

EXAMPLE 13

Preparation of
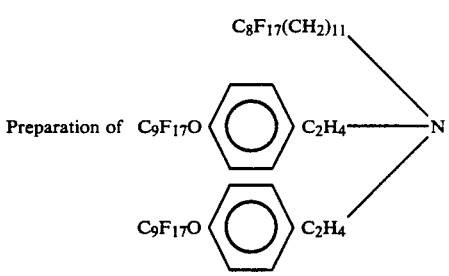

In a 1 l round-bottomed flask were placed 58.9 g (0.10 mol) of a fluoroamine represented by the formula $C_8F_{17}(CH_2)_{11}NH_2$ prepared in the synthesis of Example 1, 135.6 g (0.20 mol) of a fluoroiodide represented by the formula

and 300 ml of methyl ethyl ketone, the mixture was warmed to 70° C., and 150 ml of 10% aqueous sodium carbonate solution was added dropwise thereto with stirring over a period of about 2 hours. Thereafter, stirring was continued under reflux for 6 hours to complete the reaction. The reaction liquid was mixed with 500 ml of benzene, then the organic layer was separated and washed repeatedly with distilled water until the pH of the aqueous layer reached 7. The benzene solution was dried with anhydrous sodium sulfate, and the solvent was distilled away under reduced pressure. The resulting product was subjected to molecular distillation at 150° C. to obtain a clear liquid represented by the formula

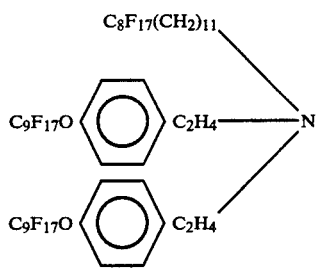

The results of GPC and organic mass spectrometry revealed that the liquid was a single component containing no starting material and no intermediate product.

EXAMPLE 14

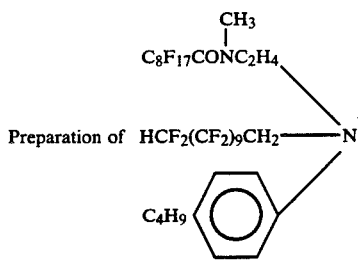

In a 1 l round-bottomed flask were placed 64.5 g (0.10 mol) of a fluoroamine represented by the formula

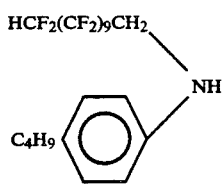

prepared in the synthesis of Example 3, 64.5 g (0.10 mol) of a fluoroiodide represented by the formula

and 300 ml of methyl ethyl ketone. The mixture was warmed to 70° C. and 150 ml of 10% aqueous sodium carbonate solution was added dropwise thereto with stirring over a period of about 2 hours. Thereafter, stirring was continued under reflux for 6 hours to complete the reaction. The reaction liquid was mixed with 600 ml of benzene, the organic layer was separated and was washed repeatedly with distilled water until the pH of the aqueous layer reached 7. The benzene solution was dried with anhydrous sodium sulfate and the solvent was distilled away under reduced pressure. The resulting product was recrystallized with acetone to obtain a white solid represented by the formula

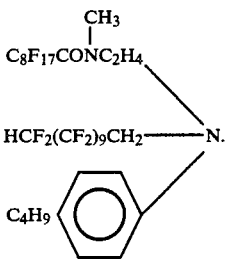

The solid was found, based on GPC and organic mass spectrometry, to be a single component containing no starting material and no intermediate product.

EXAMPLE 15

The attached drawing is a diagram showing the basic structure of a magnetic recording medium utilizing the present invention.

On the both sides of a non-magnetic support 1, are provided ferromagnetic metal thin films 2 and 2. Further, on the both sides of said ferromagnetic metal thin films 2 and 2, are provided lubricant layers 4 and 4 through the medium of carbon protective layers 3 and 3.

The above-mentioned organic compound is made to exist on the carbon protective layers, as such alone or as a mixture thereof with other lubricants, rust preventing agents, etc., in the form of thin layer at a rate of 0.05-300 mg (preferably 0.1-150 mg) per 1 m$^2$ of the surface. This may be performed by using conventional dry or wet coating methods.

The effect of the present invention can be obtained by forming a lubricant layer containing the organic compound mentioned above on a carbon protective layer. As the carbon protective layer, there may be used carbon thin films the state of amorphous carbon, graphite, diamond, the mixture thereof, or the lamination thereof, obtained by such means as sputtering and plasma CVD. The thickness of the layer is suitably 50-500 Å.

The ferromagnetic metal thin films may be those of Co-Ni, Co-Cr, Co-Ni-Cr, Co-Ni-P, Fe-Co, Fe-Co-Ni, etc. obtained by means of vacuum vapor deposition, sputtering, ion plating, plating etc. As occasion demands, underlayers of Cr, Ti, etc. may also be provided.

The thickness of the ferromagnetic metal tin film including that of the underlayer is suitably 500-5,000 Å. Between the ferromagnetic metal thin film and the carbon protective layer, there may also be formed, as occasion demands, thin film of non-magnetic metals such as Cr and Ti or organic plasma-polymerized film, etc.

The non-magnetic support may comprise as the principal material glass, ceramic, metals such as Al alloy and Ti alloy, and plastics such as polyesters, polyimides, polyamideimides, polycarbonates, and polyacrylates and, as occasion demands, may have Co-P plating film, polyimide coating, etc. formed on the surface or may be provided with protrusions made by texture finishing or protrusions in the form of fine particles, hills, waves etc. on the surface. The shape of the support may be properly selected according to intended uses including disc, sheet, film, card, drum, and so forth. The surface roughness of the support is suitably 100–600 Å in terms of the maximum height, Rmax.

Some embodiments of the present invention will be further described in detail below.

A non-magnetic substrate 1 was prepared by applying a non-magnetic Ni-P alloy plating 25 μm in thickness onto the surface of an Al alloy plate 95 mm in diameter and 1.2 mm in thickness and forming on the surface by texture finishing protrusions of a mean roughness of 50 Å and a maximum height of 300 Å. Then, a Cr underlayer of 1300 Å thickness and a Co-Ni ferromagnetic metal thin film 2 of 600 Å thickness were formed on the substrate by means of sputtering, and a graphite protective layer 3 of 200 Å thickness was further formed thereon by means of sputtering, the resulting product being named sample A. Sample B was prepared in the same manner as above but by forming a diamond-like carbon protective layer 3 of 50 Å thickness by means of plasma CVD in place of the graphite protective layer 3. Similarly, sample C was prepared by forming a diamond-like carbon protective layer 3 of 30 Å thickness and sample D by forming no carbon protective layer.

The various organic compounds described before were each separately coated on each of the above samples in an amount of 10 mg per 1 m² of the surface. These represent Experimental Examples 1 to 27. With each specimen of Experimental Examples, CSS determination and head adsorption test were made immediately after the coating and after standing at 90° C. for 24 hours. The CSS durability was evaluated in terms of the number of times of CSS at the point of time where the friction coefficient exceeded 1.0 or the number of times of CSS at the point of time where the head crash occurred, and these points of time were taken as the CSS life. In the adsorption test, the disc was allowed to stand at 60° C. for 24 hours with a slider fixed thereto and then rotated at room temperature. When the force applied to the slider at the start of the rotation showed an abnormal value, it was regarded as the occurrence of adsorption.

Table 1 shows, with respective specimens mentioned above, the details of the specimens and the results of the CSS test and the adsorption test.

In the Table, Experimental Examples 20 to 27 are Comparative Examples.

Table 1 reveals that when the organic compound has no fluoroalkyl terminal group or no fluoroaryl terminal group or the number of their carbon atoms is 2 or less (Experimental Examples 20 and 21), when the number of total carbon atoms of the hydrocarbon chain is 9 or less (Experimental Examples 22 and 23), when the polar group has a weak adhesive force as in the ester group (Experimental Example 24), or when the carbon protective layer is very thin or is lacking (Experimental Examples 25 and 26) the intended performance cannot be obtained, whereas when the above conditions are within the scope of the present invention, the results of CSS test and adsorption test are all good. On the other hand, when a perfluoropolyether known to the art was used for the lubricant layer, intended performance could not be obtained.

TABLE 1

| Example No.* | Organic compound used | Sample classification | CSS Test result (number of times) Initial | CSS Test result (number of times) After standing at high temp. | Adsorption test result |
|---|---|---|---|---|---|
| 1 | $C_6F_{13}(CH_2)_{16}COOH$ | A | ≧50,000 | ≧50,000 | ○ |
| 2 | $C_8F_{17}SO_2N(CH_2)_{12}COOH$ with $C_2H_5$ branch on N | B | ≧50,000 | ≧50,000 | ○ |
| 3 | 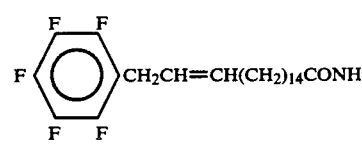 pentafluorophenyl-$CH_2CH=CH(CH_2)_{14}CONH_2$ | A | ≧50,000 | ≧50,000 | ○ |
| 4 | $HCF_2(CF_2)_9(CH_2)_{11}CONH_2$ | B | ≧50,000 | ≧50,000 | ○ |
| 5 | 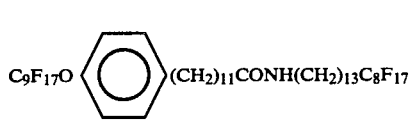 $C_9F_{17}O$-phenyl-$(CH_2)_{11}CONH(CH_2)_{13}C_8F_{17}$ | A | ≧50,000 | ≧50,000 | ○ |
| 6 | $C_6F_{13}(CH_2)_{11}CONH(CH_2)_{12}(CF_2)_7CF_2H$ | B | ≧50,000 | ≧50,000 | ○ |

TABLE 1-continued

| Example No.* | Organic compound used | Sample classification | CSS Test result (number of times) Initial | CSS Test result After standing at high temp. | Adsorption test result |
|---|---|---|---|---|---|
| 7 | (F₅-C₆H)₂CH(CH₂)₁₅CH(CH₃)CH₂NH₂ | A | ≧50,000 | ≧50,000 | ○ |
| 8 | C₉F₁₇O-C₆H₃(CH₃)-(CH₂)₇NH₂ | B | ≧50,000 | ≧50,000 | ○ |
| 9 | C₆F₁₃(CH₂)₁₂\NH/HCF₂(CF₂)₇(CH₂)₁₂ | A | ≧50,000 | ≧50,000 | ○ |
| 10 | C₉F₁₇O-C₆H₄-(CH₂)₁₂NH(CH₂)₁₃C₈F₁₇ | B | ≧50,000 | ≧50,000 | ○ |
| 11 | C₈F₁₇CON(C₂H₅)(CH₂)₁₃—N[(CH₂)₁₂(CF₂)₇CF₂H][(CH₂)₁₂C₆F₁₃] | A | ≧50,000 | ≧50,000 | ○ |
| 12 | C₉F₁₇O-C₆H₄-(CH₂)₁₂—N—(CH₂)₁₃C₈F₁₇ / (CH₂)₆-C₆H₄-OC₆F₁₁ | B | ≧50,000 | ≧50,000 | ○ |
| (20) | C₁₇H₃₅COOH | A | Crash at 10,000 | Crash at 10,000 | ○ |
| (21) | C₂F₅(CH₂)₁₆CONH₂ | B | Crash at 20,000 | Crash at 20,000 | ○ |
| (22) | C₈F₁₇(CH₂)₈COOH | A | ≧50,000 | Crash at ≧25,000 | ○ |
| (23) | C₉F₁₇O-C₆H₄-CH₂NH₂ | B | 11,000 | 5,000 | ○ |
| (24) | HCF₂(CF₂)₉(CH₂)₁₁COO(CH₂)₁₂-C₆F₅ | A | 15,000 | 15,000 | x |

TABLE 1-continued

| Example No.* | Organic compound used | Sample classification | CSS Test result (number of times) Initial | CSS Test result After standing at high temp. | Adsorption test result |
|---|---|---|---|---|---|
| (25) | $C_8F_{17}SO_2N(C_2H_5)(CH_2)_{12}COOH$ | C | Crash at 35,000 | Crash at 35,000 | ◯ |
| (26) | (C₆F₁₁O–C₆H₄–(CH₂)₆O)₃P=O | D | Crash at 15,000 | Crash at 15,000 | x |
| (27) | $F-[CF(CF_3)-CF_2-O]_n-CF(CF_3)-COOH$ (Average m.w. 3,200) | A | 21,000 | 21,000 | x |

Note:
*The numbers in parentheses refer to Comparative Examples.

EXAMPLE 16

Twenty (20) parts each of the organic fluorine compounds prepared by the methods of Examples 2 to 14 or similar methods were separately dissolved in 1000 parts of isopropanol, and 100 parts each of ferromagnetic metal (comprising α-Fe) power was added and dispersed into the respective solutions. The liquid dispersion was then filtered and dried to make the organic fluorine compound of the present invention adhere to the ferromagnetic metal powder surface. As Comparative Examples, ferromagnetic metal powders were subjected separately to the surface treatment in the same manner as described above except for using a hydrocarbon having a polar group known to the art or a surface active agent synthesized separately. These ferromagnetic metal powders (100 parts each) were added respectively to the following composition and thoroughly mixed and dispersed in a ball mill to obtain magnetic coating materials.

| | |
|---|---|
| Polyurethane | 10 parts |
| Vinyl chloride-vinyl acetate copolymer (VAGH) | 10 parts |
| Isocyanate solution (colorate L) | 5 parts |
| Tristearin | 0.1 part |
| Methyl ethyl ketone | 100 parts |
| Toluene | 80 parts |
| Cyclohexanone | 10 parts |

These coating materials were each coated and dried on a polyester film of 10 μm thickness with a magnetic field of 2000 gauss being applied thereto, to give a film thickness of 5 μm and then subjected to calendering and cutting to obtain a magnetic tape. In the present Example, to examine the dispersion stability of the coating material, coating was conducted after the coating material had been allowed to stand for 5 days after the preparation of the material. The respective tapes thus obtained were examined for RF output and video S/N on a video deck. The surface roughness of the magnetic layer was determined with a tracer-type surface roughness meter. Further, as the storage stability test, the respective tapes were allowed to stand at 60° C. and 90% R.H. for 1 month, and then used for recording and regeneration and examined for development of head clogging at the time. The results of these tests are shown in Tables 2 to 6. The tape numbers shown in parentheses in the Tables refer to comparative Examples.

TABLE 2

| Tape No. | Treating agent for magnetic powder | RF output (dB) | Video S/N (dB) | Surface roughness (μm) | Head clogging |
|---|---|---|---|---|---|
| 1 | $HCF_2(CF_2)_9(CH_2)_{11}COOH$ | +1.5 | +2.0 | 0.005 | None |
| 2 | $C_9F_{17}O(CH_2)_{20}COOH$ | +1.0 | +1.5 | 0.008 | None |

TABLE 2-continued

| Tape No. | Treating agent for magnetic powder | RF output (dB) | Video S/N (dB) | Surface roughness (μm) | Head clogging |
|---|---|---|---|---|---|
| 3 | F-C6F3-CH2CH=CH(CH2)14CONH2 | +1.5 | +2.0 | 0.006 | None |
| 4 | $HCF_2(CF_2)_3(CH_2)_{17}COOH$ | +1.5 | +2.0 | 0.005 | None |
| 5 | $C_9F_{17}O$-C6H4-CON(H)(CH2)12COOH | +1.0 | +1.5 | 0.008 | None |
| 6 | $C_9F_{17}O$-C6H3(CH3)-(CH2)6COOH | +1.0 | +1.5 | 0.008 | None |
| 7 | $C_6F_{11}O$-C6H4-(CH2)11COOH | +1.2 | +2.0 | 0.007 | None |
| 8 | (F-C6F3)2CH(CH2)15CH(CH3)COOH | +1.2 | +2.0 | 0.007 | None |
| 9 | $C_{17}H_{35}COOH$ | 0 | 0 | 0.011 | Poor |
| 10 | $HCF_2(CF_2)_{17}COOH$ | 0 | 0 | 0.010 | Poor |
| 11 | $HCF_2(CF_2)_9(CH_2)_7COOH$ | +0.1 | +0.1 | 0.010 | Poor |
| 12 | F-C6F3-(CH2)7CONH | −0.1 | −0.2 | 0.017 | Poor |

Table 2 reveals that when the fluoroalkyl terminal group or the fluoroaryl terminal group is absent or the number of total carbon atoms thereof is 2 or less [Comparative Examples 9 and 10], or when the number of total carbon atoms of the hydrocarbon chain is 9 or less [Comparative Examples 11 and 12], the intended performances cannot be obtained, whereas when the above conditions are within the scope of the present invention, the surface roughness, video deck test results, and storage test results are all good.

TABLE 3

| Tape No. | Treating agent for magnetic powder | RF output (dB) | Video S/N (dB) | Surface roughness (μm) | Head clogging |
|---|---|---|---|---|---|
| 1 | $C_8F_{17}(CF_2)_{10}CONH(CH_2)_{12}(CF_2)_9CFH$ | +1.5 | +2.0 | 0.006 | None |
| 2 | $C_9F_{17}O$-C6H3(CH3)-(CH2)6COOH | +1.2 | +1.5 | 0.008 | None |

TABLE 3-continued

| Tape No. | Treating agent for magnetic powder | RF output (dB) | Video S/N (dB) | Surface roughness (μm) | Head clogging |
|---|---|---|---|---|---|
| 3 | F-C6F4-CH11CONH(CH2)12-C6H4-OC6F11 (pentafluorophenyl—CH11CONH(CH2)12—phenyl—OC6F11) | +1.5 | +2.0 | 0.006 | None |
| 4 | $C_8F_{17}SO_2N(CH_2)_{12}CONH(CH_2)_{15}CH=CHCH_2$—C6H4F (difluorophenyl) | +1.2 | +1.5 | 0.007 | None |
| 5 | $C_6F_{13}(CH_2)_{11}CONH(CH_2)_{23}C_{10}F_{21}$ | +1.5 | +2.0 | 0.006 | None |
| 6 | (pentafluorophenyl)₂CH(CH₂)₁₅CH(CH₃)CONH(CH₂)₁₂—C₆H₄—OC₉F₁₇ | +1.0 | +1.5 | 0.008 | None |
| (7) | $C_{17}H_{55}CONHC_{12}H_{25}$ | 0 | 0 | 0.016 | Poor |
| (8) | $C_2F_5(CH_2)_{16}CONH(CH_2)_{11}C_2F_5$ | +0.2 | +0.2 | 0.011 | Poor |
| (9) | $C_8F_{17}(CH_2)_8CONHCH_2(CF_2)_9CF_2$ | 0 | +0.1 | 0.014 | Poor |
| (10) | F-C6F4-(CH2)7CONHCH2—C6H4—OC9F17 (pentafluorophenyl—(CH₂)₇CONHCH₂—phenyl—OC₉F₁₇) | −0.1 | −0.2 | 0.018 | Poor |

The results shown in Table 3 reveal that when the fluoroalkyl terminal group or the fluoroaryl terminal group is absent or the number of total carbon atoms thereof is 2 or less [Comparative Examples 7 and 8], or when the number of total carbon atoms of the hydrocarbon chain is 9 or less [Comparative Examples 9 and 10], the intended performance cannot be obtained, whereas when the above conditions are within the scope of the present invention, the surface roughness, video deck test results and storage test results are all good.

TABLE 4

| Tape No. | Treating agent for magnetic powder | RF output (dB) | Video S/N (dB) | Surface roughness (μm) | Head clogging |
|---|---|---|---|---|---|
| 1 | $HC_2(CF_2)_9(CH_2)_{12}OH$ | +1.3 | +2.0 | 0.006 | None |
| 2 | $C_9F_{17}O(CH_2)_{21}OH$ | +0.9 | +1.5 | 0.008 | None |
| 3 | (pentafluorophenyl)—CH₂CH=CH(CH₂)₁₅OH | +1.3 | +2.0 | 0.006 | None |
| 4 | $C_6F_{15}(CH_2)_{15}OH$ | +1.3 | +2.0 | 0.006 | None |
| 5 | $C_9F_{17}O$—C6H4—CON(H)(CH₂)₁₃OH | +1.0 | +1.5 | 0.007 | None |
| 6 | $C_9F_{17}O$—(methylphenyl)—(CH₂)₇OH | +0.8 | +0.3 | 0.009 | None |

TABLE 4-continued

| Tape No. | Treating agent for magnetic powder | RF output (dB) | Video S/N (dB) | Surface roughness (μm) | Head clogging |
|---|---|---|---|---|---|
| 7 | $C_6F_{11}O$—⟨phenyl⟩—$(CH_2)_{13}OH$ | +1.1 | +2.0 | 0.007 | None |
| 8 | $(C_6F_5)_2CH(CH_2)_{15}CH(CH_3)CONH(CH_2)_{12}$—⟨phenyl⟩—$OC_9F_{17}$ | +1.2 | +2.0 | 0.007 | None |
| (9) | $C_{17}H_{55}CONHC_{12}H_{25}$ | 0 | 0 | 0.013 | Poor |
| (10) | $C_2F_5(CH_2)_{16}CONH(CH_2)_{11}C_2F_5$ | 0 | 0 | 0.012 | Poor |
| (11) | $C_8F_{17}(CH_2)_8CONHCH_2(CF_2)_9CF_2$ | 0 | | 0.012 | Poor |

The results shown in Table 4 reveal that when the fluoroalkyl terminal group or the fluoroaryl terminal group is absent [Comparative Examples 9 and 10] or the number of carbon atoms thereof is 9 or less [comparative Example 11], the intended performance cannot be obtained, whereas when the above conditions are within the scope of the present invention, the surface roughness, video deck test results, and storage test results are all good.

TABLE 5

| Tape No. | Treating agent for magnetic powder | RF output (dB) | Video S/N (dB) | Surface roughness (μm) | Head clogging |
|---|---|---|---|---|---|
| 1 | $C_8F_{17}(CH_2)_{10}CONH_2$ | +1.2 | +1.5 | 0.008 | None |
| 2 | $C_9F_{17}O$—⟨phenyl⟩—$(CH_2)_6CONH_2$ | +1.0 | +1.5 | 0.008 | None |
| 3 | $HCF_2(CF_2)_9(CH_2)_5CONH_2$ | +1.6 | +2.0 | 0.007 | None |
| 4 | $(C_6F_5)CH_2CH=CH(CH_2)_{14}OH$ | +1.6 | +2.0 | 0.006 | None |
| 5 | $(C_6F_5)_2CH(CH_2)_{15}CH(CH_3)CONH_2$ | +1.2 | +2.0 | 0.007 | None |
| 6 | $C_8F_{17}SO_2N(C_2H_5)CH_2CONH_2$ | +1.0 | +1.5 | 0.008 | None |
| 7 | $C_9F_{17}O$—⟨phenyl⟩—$CON(H)(CH_2)_{12}CONH_2$ | +1.2 | +2.0 | 0.008 | None |

TABLE 5-continued

| Tape No. | Treating agent for magnetic powder | RF output (dB) | Video S/N (dB) | Surface roughness (μm) | Head clogging |
|---|---|---|---|---|---|
| (8) | Stearic acid | 0 | 0 | 0.011 | Poor |

TABLE 6

| Tape No. | Treating agent for magnetic powder | RF output (dB) | Video S/N (dB) | Surface roughness (μm) | Head clogging |
|---|---|---|---|---|---|
| 1 | $C_8F_{17}(CH_2)_{11}NH_2$ | +1.5 | +1.5 | 0.008 | None |
| 2 | $C_9F_{17}O(CH_2)_6NH_2$ | +1.2 | +2.0 | 0.007 | None |
| 3 | 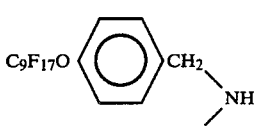 | +1.5 | +2.0 | 0.008 | None |
| 4 | 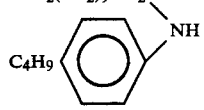 | +1.2 | +2.0 | 0.007 | None |
| 5 | 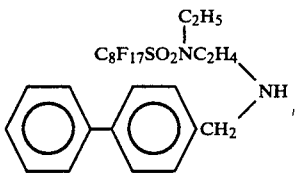 | +1.2 | +2.0 | 0.007 | None |
| 6 | 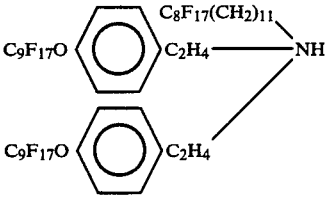 | +1.5 | +2.0 | 0.008 | None |
| 7 | 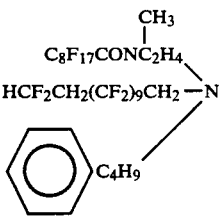 | +1.0 | +1.5 | 0.008 | None |
| (8) | Stearic acid | 0 | 0 | 0.011 | Poor |

EXAMPLE 17

A magnetic layer of 3 μm thickness comprising Co-containing $\gamma$-$Fe_2O_3$ magnetic powders dispersed thereon was formed on the surface of polyester film of 10 μm thickness. Then, various kinds of back coating were formed on the backside of the film in the following manner. The surface active agents used in Example 4 and the surface active agents used in Comparative Example were each separately added to the following composition in an amount of 2 parts each and the resulting mixtures were separately dispersed in a ball mill for 15 hours to prepare back coating liquids.

| | |
|---|---|
| Fluorocarbon resin powder ("Lubron", particle diameter 0.3 m) | 20 parts |
| Carbon black | 20 parts |
| Calcium carbonate | 40 parts |
| Polyester resin | 20 parts |
| Methyl ethyl ketone | 300 parts |
| Toluene | 200 parts |
| Cyclohexanone | 50 parts |

Ten (10) days after the preparation of the coating liquids, the liquids were each separately coated to form back coating layers of 0.5 μm thickness. The coated films were then cut to obtain magnetic tapes. These tapes were run on a video deck to examine the initial video S/N and the state of abrasion of the backside after 100 passes. Separately, the initial surface roughness of the tape was determined. The results of these tests are shown in Tables 7 to 11. The tape numbers shown in parentheses in the Tables refer to Comparative Examples.

The results shown in Table 7 reveal that when the fluoroalkyl terminal group or the fluoroacryl terminal group is absent or the number of carbon atoms thereof is 2 or less (Comparative Examples 21 and 22), or when the number of total carbon atoms of the hydrocarbon chain is 9 or less (comparative Examples 23 and 24), the intended performance cannot be obtained, whereas when the above conditions are within the scope of the present invention, the source roughness, video deck test results, and abrasion test results are all good.

TABLE 7

| Tape No. | Surface active agent | Video S/N (dB) | Abrasion state (after 100 pass) | Surface roughness (μm) |
|---|---|---|---|---|
| 13 | The one used in No. 1, Tab. 2 | +1.0 | Good | 0.03 |
| 14 | The one used in No. 2, Tab. 2 | +0.8 | Good | 0.05 |
| 15 | The one used in No. 3, Tab. 2 | +1.0 | Good | 0.03 |
| 16 | The one used in No. 4, Tab. 2 | +1.0 | Good | 0.03 |
| 17 | The one used in No. 5, Tab. 2 | +0.8 | Good | 0.05 |
| 18 | The one used in No. 6, Tab. 2 | +0.8 | Good | 0.05 |
| 19 | The one used in No. 7, Tab. 2 | +1.0 | Good | 0.04 |
| 20 | The one used in No. 8, Tab. 1 | +1.0 | Good | 0.04 |
| (21) | The one used in No. 9, Tab. 1 | 0 | Poor | 1.0 |
| (22) | The one used in No. 10, Tab. 1 | 0 | Poor | 1.0 |
| (23) | The one used in No. 11, Tab. 1 | 0 | Poor | 1.1 |
| (24) | The one used in No. 12, Tab. 1 | 0 | Poor | 1.4 |

TABLE 8

| Tape No. | Surface active agent | Video S/N (dB) | Abrasion state (after 100 pass) | Surface roughness (μm) |
|---|---|---|---|---|
| 11 | The one used in No. 1, Tab. 3 | +0.8 | Good | 0.05 |
| 12 | The one used in No. 2, Tab. 3 | +0.8 | Good | 0.05 |
| 13 | The one used in No. 3, Tab. 3 | +1.0 | Good | 0.04 |
| 14 | The one used in No. 4, Tab. 3 | +0.8 | Good | 0.05 |
| 15 | The one used in No. 5, Tab. 3 | +1.0 | Good | 0.04 |
| 16 | The one used in No. 6, Tab. 3 | +0.8 | Good | 0.05 |
| (17) | The one used in No. 7, Tab. 3 | 0 | Poor | 1.2 |
| (18) | The one used in No. 8, Tab. 3 | 0 | Poor | 1.1 |
| (19) | The one used in No. 9, Tab. 3 | 0 | Poor | 1.2 |
| (20) | The one used in No. 10, Tab. 3 | 0 | Poor | 1.3 |

The results shown in Table 8 reveal that when the fluoroalkyl terminal group or the fluoroaryl terminal group is absent or the number of carbon atoms thereof is 2 or less (Comparative Examples 19 and 20), the intended performances cannot be obtained, whereas when the above conditions are within the scope of the present invention, the surface roughness, video deck test results, and abrasion test results are all good.

TABLE 9

| Tape No. | Surface active agent | Video S/N (dB) | Abrasion state (after 100 pass) | Surface roughness (μm) |
|---|---|---|---|---|
| 13 | The one used in No. 1, Tab. 4 | +1.0 | Good | 0.03 |
| 14 | The one used in No. 2, Tab. 4 | +0.9 | Good | 0.05 |
| 15 | The one used in No. 3, Tab. 4 | +0.8 | Good | 0.05 |
| 16 | The one used in No. 4, Tab. 4 | +1.0 | Good | 0.03 |
| 17 | The one used in No. 5, Tab. 4 | +1.0 | Good | 0.03 |
| 18 | The one used in No. 6, Tab. 4 | +0.8 | Good | 0.05 |
| 19 | The one used in No. 7, Tab. 4 | +0.8 | Good | 0.06 |
| 20 | The one used in No. 8, Tab. 4 | +1.0 | Good | 0.03 |
| (21) | The one used in No. 9, Tab. 4 | 0 | Poor | 1.1 |
| (22) | The one used in No. 10, Tab. 4 | 0 | Poor | 1.0 |
| (23) | The one used in No. 11, Tab. 4 | 0 | Poor | 1.0 |

Table 9 reveals that when the fluoroalkyl terminal group or the fluoroaryl terminal group is absent or the number of carbon atoms thereof is 2 or less (Comparative Examples 21 and 22), or when the number of total carbon atoms of the hydrocarbon chain is 9 or less (Comparative Example 23), the intended performance cannot be obtained, whereas when the above conditions are within the scope of the present invention, the surface roughness, video deck test results, and abrasion test results are all good.

TABLE 10

| Tape No. | Surface active agent | Video S/N (dB) | Abrasion state (after 100 pass) | Surface roughness (μm) |
|---|---|---|---|---|
| 9 | The one used in No. 1, Tab. 5 | +0.8 | Good | 0.05 |
| 10 | The one used in No. 2, Tab. 5 | +0.8 | Good | 0.05 |
| 11 | The one used in No. 3, Tab. 5 | +1.0 | Good | 0.04 |
| 12 | The one used in No. 4, Tab. 5 | +1.0 | Good | 0.04 |
| 13 | The one used in No. 5, Tab. 5 | +0.8 | Good | 0.05 |
| 14 | The one used in No. 6, Tab. 5 | +0.8 | Good | 0.05 |
| 15 | The one used in No. 7, Tab. 5 | +1.0 | Good | 0.05 |
| (16) | Stearic acid | 0 | Poor | 1.0 |

TABLE 11

| Tape No. | Surface active agent | Video S/N (dB) | Abrasion state (after 100 pass) | Surface roughness (μm) |
|---|---|---|---|---|
| 9 | The one used in No. 1, Tab. 6 | +0.8 | Good | 0.05 |
| 10 | The one used in No. 2, Tab. 6 | +0.8 | Good | 0.05 |
| 11 | The one used in No. 3, Tab. 6 | +1.0 | Good | 0.04 |
| 12 | The one used in No. 4, Tab. 6 | +1.0 | Good | 0.05 |
| 13 | The one used in No. 5, Tab. 6 | +1.0 | Good | 0.05 |

TABLE 11-continued

| Tape No. | Surface active agent | Video S/N (dB) | Abrasion state (after 100 pass) | Surface roughness (μm) |
|---|---|---|---|---|
| 14 | The one used in No. 6, Tab. 6 | +0.8 | Good | 0.04 |
| 15 | The one used in No. 7, Tab. 6 | +0.8 | Good | 0.05 |
| (16) | Stearic acid | 0 | Poor | 1.0 |

EFFECT OF THE INVENTION

The organic fluorine compound of the present invention is capable of greatly improving the dispersibility of magnetic powders in magnetic coating materials, has also an excellent rust prevention effect on metallic magnetic powders, and exhibits in the present invention a marked dispersing effect even on fluorocarbon resin fine powders, which can be difficultly dispersed with conventional dispersing agents. Moreover, the organic fluorine compound of the present invention exhibits superior performance as a metal surface treating agent, fiber surface treating agent, resin modifiers etc. excellent in water repellency, oil repellency, soil resistance, mold release, rust prevention etc. to those of the prior art. Further, when used in magnetic recording media, the organic fluorine compound of the present invention enables manifestation of good endurance reliability while retaining such performance as CSS durability and head adsorption property, even when the height of surface protrusions is reduced and the surface flatness is thereby considerably enhanced for the purpose of increasing the recording density. Thus, the present invention is of great industrial advantage.

What is claimed is:

1. An organic fluorine compound represented by the general formula

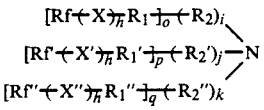

wherein Rf, Rf′, and Rf″ respectively denote a fluoroalkyl terminal group of a carbon number of 3 or more, a fluoroalkenyl terminal group of a carbon number of 3 or more, or a fluoroaryl terminal group; X, X′, and X″ respectively denote a linking group selected from $-O-$, $-CON(R_3)-$ and $-SO_2N(R_3)-$, (wherein $R_3$ denote hydrogen atom, methyl group or ethyl group); h denotes 0 or 1; $R_1$, $R_1'$ and $R_1''$ respectively denote an aliphatic alkylene group or a phenylene group having an alkylene group, and $R_2$, $R_2'$ and $R_2''$ denote hydrogen atom, an aryl group or an aliphatic alkyl group; at least one group of said $R_1$, $R_1'$ and $R_1''$, $R_2$, $R_2'$ and $R_2''$ having a total carbon number of 10 or more; and o, p, q, i, j and k each denote 0 or 1, with the proviso that $o+i=p+j=q+k=1$ and $o+p+q \geq 1$.

* * * * *